US009566443B2

(12) United States Patent
de Canniere (10) Patent No.: US 9,566,443 B2
(45) Date of Patent: Feb. 14, 2017

(54) SYSTEM FOR TREATING HEART VALVE MALFUNCTION INCLUDING MITRAL REGURGITATION

(71) Applicant: CorQuest Medical, Inc., Mont-Saint-Guibert (BE)

(72) Inventor: Didier de Canniere, Miami Beach, FL (US)

(73) Assignee: CorQuest Medical, Inc., Mont-Saint-Guibert (BE)

( * ) Notice: Subject to any disclaimer, the term of this patent is extended or adjusted under 35 U.S.C. 154(b) by 378 days.

(21) Appl. No.: 14/090,383

(22) Filed: Nov. 26, 2013

(65) Prior Publication Data

US 2015/0148590 A1    May 28, 2015

(51) Int. Cl.
*A61F 2/24*  (2006.01)
*A61N 1/368*  (2006.01)
(Continued)

(52) U.S. Cl.
CPC ............ *A61N 1/368* (2013.01); *A61M 1/1068* (2013.01); *A61N 1/0587* (2013.01); *A61N 1/0597* (2013.01); *A61N 1/3684* (2013.01)

(58) Field of Classification Search
CPC ............ A61F 2/02; A61F 2/24; A61F 2/2478; A61F 2/2481; A61N 1/368
(Continued)

(56) References Cited

U.S. PATENT DOCUMENTS 3,587,567 A * 6/1971 Schiff ................. A61M 1/1068
                                                                601/153
4,536,893 A * 8/1985 Parravicini ......... A61M 1/1068
                                                                601/153
(Continued)

FOREIGN PATENT DOCUMENTS

EP           0577400 B1    10/1999
EP           1147743       10/2001
(Continued)

OTHER PUBLICATIONS

Mike Blaber, Metals, Non-Metals, and Metalloids, http://www.mikeblaber.org/oldwine/chm 1045/notes/Periodic/Metals/Period06.htm, 1996, accessed May 14, 2015.

*Primary Examiner* — Samuel Gilbert
(74) *Attorney, Agent, or Firm* — Wolf, Greenfield & Sacks, P.C.

(57) ABSTRACT

A system for treating heart valve malfunction specifically including mitral regurgitation including a positioning structure operative to assume both expanded and contracted orientations and a retaining assembly positioned and structured to operatively dispose the positioning structure in moveably supporting lifting and/or positioning relation to the ventricular wall portion of the heart. The retaining assembly and the positioning structure are cooperatively disposed and structured to accomplish a shape variance of the heart upon a lifting or positioning force being exerted thereon substantially concurrent to the positioning structure being disposed in the expanded orientation. The force
(Continued)

exerted on the heart at least partially defines a shape variance thereof to the extent of positioning of the leaflets of the mitral valve into a closed orientation which restricts mitral regurgitation.

27 Claims, 5 Drawing Sheets (51) Int. Cl.
  *A61M 1/10* (2006.01)
  *A61N 1/05* (2006.01)
(58) Field of Classification Search
  USPC .............................................. 600/16–18, 37
  See application file for complete search history.

(56) References Cited

U.S. PATENT DOCUMENTS

| | | | |
|---|---|---|---|
| 4,690,134 A * | 9/1987 | Snyders | A61M 1/1068 601/153 |
| 5,201,742 A | 4/1993 | Hasson | |
| 5,591,170 A | 1/1997 | Spievack et al. | |
| 5,702,421 A | 12/1997 | Schneidt | |
| 6,063,070 A | 5/2000 | Eder | |
| 6,206,907 B1 | 3/2001 | Marino et al. | |
| 6,328,757 B1 | 12/2001 | Matheny | |
| 6,425,911 B1 | 7/2002 | Akerfeldt et al. | |
| 6,508,828 B1 | 1/2003 | Akerfeldt et al. | |
| 6,537,290 B2 | 3/2003 | Adams et al. | |
| 6,596,012 B2 | 7/2003 | Akerfeldt et al. | |
| 6,616,596 B1 * | 9/2003 | Milbocker | A61M 1/1037 600/16 |
| 6,641,592 B1 | 11/2003 | Sauer | |
| 6,682,489 B2 | 1/2004 | Tenerz et al. | |
| 6,712,837 B2 | 3/2004 | Åkerfeldt et al. | |
| 6,902,522 B1 * | 6/2005 | Walsh | A61F 2/2481 600/16 |
| 6,929,655 B2 | 8/2005 | Egnelöv et al. | |
| 6,960,220 B2 | 11/2005 | Marino et al. | |
| 7,044,916 B2 | 5/2006 | Tenerz et al. | |
| 7,445,626 B2 | 11/2008 | Songer | |
| 8,092,363 B2 * | 1/2012 | Leinsing | A61F 2/2481 600/16 |
| 8,133,168 B2 * | 3/2012 | Monnet | A61F 2/2481 600/16 |
| 8,147,542 B2 | 4/2012 | Maisano et al. | |
| 8,408,214 B2 | 4/2013 | Spenser | |
| 8,506,624 B2 | 8/2013 | Vidlund | |
| 8,758,393 B2 | 6/2014 | Zentgraf | |
| 8,790,394 B2 | 7/2014 | Miller | |
| 2002/0100485 A1 | 8/2002 | Stevens et al. | |
| 2002/0161378 A1 | 10/2002 | Downing | |
| 2003/0120337 A1 | 6/2003 | Van Tassel et al. | |
| 2004/0087831 A1 | 5/2004 | Michels et al. | |
| 2004/0102804 A1 | 5/2004 | Chin | |
| 2004/0106945 A1 | 6/2004 | Thramann et al. | |
| 2004/0116897 A1 | 6/2004 | Aboul-Hosn | |
| 2004/0138526 A1 | 7/2004 | Guenst | |
| 2005/0137700 A1 | 6/2005 | Spence | |
| 2005/0149108 A1 | 7/2005 | Cox | |
| 2006/0074484 A1 | 4/2006 | Huber | |
| 2006/0135962 A1 | 6/2006 | Kick et al. | |
| 2006/0247672 A1 | 11/2006 | Vidlund et al. | |
| 2007/0055206 A1 | 3/2007 | To | |
| 2007/0135826 A1 | 6/2007 | Zaver et al. | |
| 2007/0162066 A1 | 7/2007 | Lyon | |
| 2007/0239108 A1 | 10/2007 | Albrecht et al. | |
| 2007/0265643 A1 | 11/2007 | Beane et al. | |
| 2008/0033241 A1 | 2/2008 | Peh et al. | |
| 2008/0114342 A1 | 5/2008 | Whayne et al. | |
| 2008/0275295 A1 | 11/2008 | Gertner | |
| 2009/0005800 A1 | 1/2009 | Franer | |
| 2009/0105751 A1 | 4/2009 | Zentgraf | |
| 2009/0192598 A1 | 7/2009 | Lattouf | |
| 2010/0042147 A1 | 2/2010 | Janovsky | |
| 2010/0161042 A1 | 6/2010 | Maisano et al. | |
| 2010/0161043 A1 | 6/2010 | Maisano | |
| 2010/0179574 A1 | 7/2010 | Longoria et al. | |
| 2010/0228077 A1 | 9/2010 | Lenker et al. | |
| 2010/0274091 A1 | 10/2010 | Rothstein et al. | |
| 2011/0029071 A1 | 2/2011 | Zlotnick et al. | |
| 2011/0060182 A1 | 3/2011 | Kassab et al. | |
| 2011/0166413 A1 | 7/2011 | Alferness | |
| 2011/0190811 A1 | 8/2011 | Shanley | |
| 2012/0143209 A1 | 6/2012 | Brecheen et al. | |
| 2012/0272452 A1 | 11/2012 | Schultz | |
| 2012/0272495 A1 | 11/2012 | Hildebrandt et al. | |
| 2012/0272497 A1 | 11/2012 | Smith | |
| 2012/0272499 A1 | 11/2012 | Schley et al. | |
| 2012/0272523 A1 | 11/2012 | Calla et al. | |
| 2012/0272555 A1 | 11/2012 | Heath | |
| 2012/0272556 A1 | 11/2012 | Brown | |
| 2012/0272595 A1 | 11/2012 | Gallant | |
| 2012/0272603 A1 | 11/2012 | Carbines | |
| 2012/0272611 A1 | 11/2012 | Tsukimoto et al. | |
| 2012/0272624 A1 | 11/2012 | Argeriou et al. | |
| 2012/0272632 A1 | 11/2012 | Lans | |
| 2012/0272637 A1 | 11/2012 | Holland et al. | |
| 2012/0272652 A1 | 11/2012 | Nicholls et al. | |
| 2012/0272653 A1 | 11/2012 | Merrill et al. | |
| 2012/0272660 A1 | 11/2012 | Garrett | |
| 2012/0272661 A1 | 11/2012 | Milburn | |
| 2012/0272662 A1 | 11/2012 | Milburn | |
| 2012/0272667 A1 | 11/2012 | Ferraro et al. | |
| 2012/0272670 A1 | 11/2012 | Choi et al. | |
| 2012/0272705 A1 | 11/2012 | Hirane | |
| 2012/0272738 A1 | 11/2012 | Klessel et al. | |
| 2012/0272741 A1 | 11/2012 | Xiao et al. | |
| 2012/0272768 A1 | 11/2012 | Schmidt et al. | |
| 2012/0272780 A1 | 11/2012 | Schimings et al. | |
| 2012/0272815 A1 | 11/2012 | Lingel et al. | |
| 2012/0272817 A1 | 11/2012 | Lindh, Sr. et al. | |
| 2012/0272841 A1 | 11/2012 | Heymanns et al. | |
| 2012/0272843 A1 | 11/2012 | Graff | |
| 2012/0272845 A1 | 11/2012 | Loiret-Bernal et al. | |
| 2012/0272846 A1 | 11/2012 | Fleischer et al. | |
| 2012/0272876 A1 | 11/2012 | Bergeron et al. | |
| 2012/0272893 A1 | 11/2012 | Lauerhaas et al. | |
| 2012/0272968 A1 | 11/2012 | Kirschner | |
| 2012/0272996 A1 | 11/2012 | Jimenez et al. | |
| 2012/0273014 A1 | 11/2012 | Tadayon | |
| 2012/0273064 A1 | 11/2012 | Ismert et al. | |
| 2012/0273078 A1 | 11/2012 | Hawwa et al. | |
| 2012/0273079 A1 | 11/2012 | Guclucan | |
| 2012/0273141 A1 | 11/2012 | Miller et al. | |
| 2012/0273142 A1 | 11/2012 | Miller et al. | |
| 2012/0273143 A1 | 11/2012 | Fillmore et al. | |
| 2012/0273161 A1 | 11/2012 | Raver | |
| 2012/0273174 A1 | 11/2012 | Barnes | |
| 2012/0273178 A1 | 11/2012 | Wanni et al. | |
| 2012/0273209 A1 | 11/2012 | Austin et al. | |
| 2012/0273210 A1 | 11/2012 | Arizmendi, Jr. et al. | |
| 2012/0273214 A1 | 11/2012 | Donald et al. | |
| 2012/0273219 A1 | 11/2012 | Hoffman et al. | |
| 2012/0273220 A1 | 11/2012 | Ezekiel et al. | |
| 2012/0273228 A1 | 11/2012 | Allouche | |
| 2012/0273230 A1 | 11/2012 | Patterson et al. | |
| 2012/0273231 A1 | 11/2012 | Whiddon | |
| 2012/0273232 A1 | 11/2012 | O'Blenes | |
| 2012/0273328 A1 | 11/2012 | Sejourne | |
| 2012/0273358 A1 | 11/2012 | Lamoy et al. | |
| 2012/0273389 A1 | 11/2012 | Aziz et al. | |
| 2012/0273399 A1 | 11/2012 | Daboub et al. | |
| 2012/0273438 A1 | 11/2012 | Nordin et al. | |
| 2012/0273439 A1 | 11/2012 | Beavers et al. | |
| 2012/0273458 A1 | 11/2012 | Bret et al. | |
| 2012/0273467 A1 | 11/2012 | Baxter et al. | |
| 2012/0273470 A1 | 11/2012 | Zediker et al. | |
| 2012/0273518 A1 | 11/2012 | Greer, Jr. | |
| 2012/0273555 A1 | 11/2012 | Flak et al. | |
| 2012/0273580 A1 | 11/2012 | Warren et al. | |
| 2012/0273641 A1 | 11/2012 | Gorman et al. | |

(56) References Cited

U.S. PATENT DOCUMENTS

| | | |
|---|---|---|
| 2012/0273647 A1 | 11/2012 | Moruzzi |
| 2012/0273680 A1 | 11/2012 | Furry |
| 2012/0273843 A1 | 11/2012 | Kim |
| 2012/0273860 A1 | 11/2012 | Chen et al. |
| 2012/0273880 A1 | 11/2012 | Teng et al. |
| 2012/0273902 A1 | 11/2012 | Lin et al. |
| 2012/0273955 A1 | 11/2012 | Or-Bach et al. |
| 2012/0273987 A1 | 11/2012 | Belcher et al. |
| 2012/0273989 A1 | 11/2012 | Graf |
| 2012/0273993 A1 | 11/2012 | Shoeeyov et al. |
| 2012/0274001 A1 | 11/2012 | Prabhu |
| 2012/0274020 A1 | 11/2012 | Daboub |
| 2012/0274061 A1 | 11/2012 | Wilkinson |
| 2012/0274065 A1 | 11/2012 | Knapp |
| 2012/0274068 A1 | 11/2012 | Hanback |
| 2012/0274076 A1 | 11/2012 | Kelaiditis et al. |
| 2012/0274145 A1 | 11/2012 | Taddeo |
| 2012/0274198 A1 | 11/2012 | Jenek |
| 2012/0274202 A1 | 11/2012 | Komatsu |
| 2012/0274212 A1 | 11/2012 | Yu et al. |
| 2012/0274256 A1 | 11/2012 | O'Rourke |
| 2012/0274266 A1 | 11/2012 | Yip |
| 2012/0274279 A1 | 11/2012 | Banos et al. |
| 2012/0274280 A1 | 11/2012 | Yip et al. |
| 2012/0274281 A1 | 11/2012 | Kim |
| 2012/0274288 A1 | 11/2012 | Wegener |
| 2012/0274332 A1 | 11/2012 | Sinha et al. |
| 2012/0274391 A1 | 11/2012 | Kim |
| 2012/0274395 A1 | 11/2012 | Deam |
| 2012/0274440 A1 | 11/2012 | Meadows et al. |
| 2012/0274470 A1 | 11/2012 | Sandvick |
| 2012/0274477 A1 | 11/2012 | Prammer |
| 2012/0274769 A1 | 11/2012 | Lee |
| 2012/0274770 A1 | 11/2012 | Lee |
| 2012/0274772 A1 | 11/2012 | Fosburgh et al. |
| 2012/0274870 A1 | 11/2012 | Liu |
| 2012/0274937 A1 | 11/2012 | Hays et al. |
| 2012/0274962 A1 | 11/2012 | Thomas et al. |
| 2012/0275056 A1 | 11/2012 | McGuire, Jr. |
| 2012/0275057 A1 | 11/2012 | McGuire, Jr. |
| 2012/0275085 A1 | 11/2012 | Wilson et al. |
| 2012/0275128 A1 | 11/2012 | Takada et al. |
| 2012/0275140 A1 | 11/2012 | Feinbloom et al. |
| 2012/0275236 A1 | 11/2012 | Hess et al. |
| 2012/0275244 A1 | 11/2012 | Do |
| 2012/0275247 A1 | 11/2012 | Hwang et al. |
| 2012/0275248 A1 | 11/2012 | Won |
| 2012/0275249 A1 | 11/2012 | Yang et al. |
| 2012/0275298 A1 | 11/2012 | Bryant et al. |
| 2012/0275299 A1 | 11/2012 | Taylor et al. |
| 2012/0275338 A1 | 11/2012 | Filsfils et al. |
| 2012/0275356 A1 | 11/2012 | Aharony et al. |
| 2012/0275670 A1 | 11/2012 | Joglekar |
| 2012/0275754 A1 | 11/2012 | Krampotich et al. |
| 2012/0275841 A1 | 11/2012 | Jimenez et al. |
| 2012/0275843 A1 | 11/2012 | Jimenez et al. |
| 2012/0275845 A1 | 11/2012 | Etling |
| 2012/0275860 A1 | 11/2012 | Exline |
| 2012/0275861 A1 | 11/2012 | Myslowski et al. |
| 2012/0275862 A1 | 11/2012 | Vitale |
| 2012/0275881 A1 | 11/2012 | Mueller |
| 2012/0275913 A1 | 11/2012 | Robertson, Jr. et al. |
| 2012/0275924 A1 | 11/2012 | Perkinson |
| 2012/0275927 A1 | 11/2012 | Rhim |
| 2012/0275970 A1 | 11/2012 | Nash et al. |
| 2012/0275999 A1 | 11/2012 | Bell et al. |
| 2012/0276005 A1 | 11/2012 | Yang et al. |
| 2012/0276008 A1 | 11/2012 | Walkenhorst et al. |
| 2012/0276009 A1 | 11/2012 | Pfeifer et al. |
| 2012/0276011 A1 | 11/2012 | Kupussamy et al. |
| 2012/0276021 A1 | 11/2012 | Kumar et al. |
| 2012/0276025 A1 | 11/2012 | Florence et al. |
| 2012/0276041 A1 | 11/2012 | Salamone et al. |
| 2012/0276053 A1 | 11/2012 | Kim |
| 2012/0276061 A1 | 11/2012 | Grazia et al. |
| 2012/0276062 A1 | 11/2012 | Kellar et al. |
| 2012/0276064 A1 | 11/2012 | Blau et al. |
| 2012/0276067 A1 | 11/2012 | Westenfelder |
| 2012/0276068 A1 | 11/2012 | Sabaawy |
| 2012/0276069 A1 | 11/2012 | Karperien et al. |
| 2012/0276071 A1 | 11/2012 | Fraser, Jr. |
| 2012/0276073 A1 | 11/2012 | Schachner et al. |
| 2012/0276074 A1 | 11/2012 | Scharenberg et al. |
| 2012/0276080 A1 | 11/2012 | Kinoshita et al. |
| 2012/0276084 A1 | 11/2012 | Schaumberg et al. |
| 2012/0276087 A1 | 11/2012 | Schafer et al. |
| 2012/0276088 A1 | 11/2012 | El-Deiry et al. |
| 2012/0276089 A1 | 11/2012 | Lee et al. |
| 2012/0276101 A1 | 11/2012 | Kwak et al. |
| 2012/0276103 A1 | 11/2012 | Karperien et al. |
| 2012/0276104 A1 | 11/2012 | Woisetschlager |
| 2012/0276110 A1 | 11/2012 | Simard |
| 2012/0276111 A1 | 11/2012 | Hafezi-Moghadam |
| 2012/0276126 A1 | 11/2012 | Varadhachary et al. |
| 2012/0276130 A1 | 11/2012 | Margarit Y Ros et al. |
| 2012/0276139 A1 | 11/2012 | Moormann et al. |
| 2012/0276143 A1 | 11/2012 | O'Mahony et al. |
| 2012/0276144 A1 | 11/2012 | Kernodle et al. |
| 2012/0276149 A1 | 11/2012 | Littman et al. |
| 2012/0276150 A1 | 11/2012 | Lauritzen et al. |
| 2012/0276151 A1 | 11/2012 | Lewis et al. |
| 2012/0276152 A1 | 11/2012 | Hossainy et al. |
| 2012/0276161 A1 | 11/2012 | Gravagna et al. |
| 2012/0276164 A1 | 11/2012 | Tuominen et al. |
| 2012/0276169 A1 | 11/2012 | Kang et al. |
| 2012/0276173 A1 | 11/2012 | Marcum et al. |
| 2012/0276182 A1 | 11/2012 | Baker, Jr. et al. |
| 2012/0276185 A1 | 11/2012 | Hossainy et al. |
| 2012/0276188 A1 | 11/2012 | Barrows |
| 2012/0276189 A1 | 11/2012 | Johnson |
| 2012/0276193 A1 | 11/2012 | Graversen et al. |
| 2012/0276201 A1 | 11/2012 | Trachtman |
| 2012/0276202 A1 | 11/2012 | Selim et al. |
| 2012/0276203 A1 | 11/2012 | Selim et al. |
| 2012/0276204 A1 | 11/2012 | Remington et al. |
| 2012/0276213 A1 | 11/2012 | Chen |
| 2012/0276218 A1 | 11/2012 | Jung et al. |
| 2012/0276232 A1 | 11/2012 | Marczyk et al. |
| 2012/0276237 A1 | 11/2012 | Heymanns et al. |
| 2012/0276278 A1 | 11/2012 | Qiu et al. |
| 2012/0276286 A1 | 11/2012 | Vijayakumar |
| 2012/0276296 A1 | 11/2012 | Fieberg et al. |
| 2012/0276297 A1 | 11/2012 | Cypcar et al. |
| 2012/0276304 A1 | 11/2012 | Derrien |
| 2012/0276330 A1 | 11/2012 | Durney et al. |
| 2012/0276365 A1 | 11/2012 | Petuskey et al. |
| 2012/0276375 A1 | 11/2012 | Colgan et al. |
| 2012/0276381 A1 | 11/2012 | Cypcar |
| 2012/0276427 A1 | 11/2012 | Kim |
| 2012/0276463 A1 | 11/2012 | Grannell et al. |
| 2012/0276465 A1 | 11/2012 | Paganelli |
| 2012/0276469 A1 | 11/2012 | Shizuku |
| 2012/0276509 A1 | 11/2012 | Iannotti et al. |
| 2012/0276518 A1 | 11/2012 | Gillis |
| 2012/0276522 A1 | 11/2012 | Huang et al. |
| 2012/0276528 A1 | 11/2012 | Cargill et al. |
| 2012/0276529 A1 | 11/2012 | Galisson et al. |
| 2012/0276537 A1 | 11/2012 | Kühn et al. |
| 2012/0276552 A1 | 11/2012 | Lu |
| 2012/0276553 A1 | 11/2012 | Gronthos et al. |
| 2012/0276554 A1 | 11/2012 | Gutteridge et al. |
| 2012/0276555 A1 | 11/2012 | Kuhn et al. |
| 2012/0276558 A1 | 11/2012 | Soper et al. |
| 2012/0276572 A1 | 11/2012 | Shekdar et al. |
| 2012/0276581 A1 | 11/2012 | Arav et al. |
| 2012/0276588 A1 | 11/2012 | Hallen-Adams et al. |
| 2012/0276591 A1 | 11/2012 | Kneissel et al. |
| 2012/0276618 A1 | 11/2012 | Dayton et al. |
| 2012/0276626 A1 | 11/2012 | Shogbon et al. |
| 2012/0276627 A1 | 11/2012 | Kelnar et al. |
| 2012/0276628 A1 | 11/2012 | Khen et al. |
| 2012/0276632 A1 | 11/2012 | Strunk et al. |
| 2012/0276679 A1 | 11/2012 | Wu |
| 2012/0276694 A1 | 11/2012 | Koezuka et al. |

(56) References Cited

U.S. PATENT DOCUMENTS

| | | |
|---|---|---|
| 2012/0276754 A1 | 11/2012 | Cordingley et al. |
| 2012/0276887 A1 | 11/2012 | Romine et al. |
| 2012/0276928 A1 | 11/2012 | Shutter |
| 2012/0277006 A1 | 11/2012 | Kim |
| 2012/0277008 A1 | 11/2012 | Kitchen et al. |
| 2012/0277051 A1 | 11/2012 | Cooper et al. |
| 2012/0277073 A1 | 11/2012 | Bartsch |
| 2012/0277093 A1 | 11/2012 | Andrew et al. |
| 2012/0277110 A1 | 11/2012 | Andre et al. |
| 2012/0277111 A1 | 11/2012 | Crabtree et al. |
| 2012/0277112 A1 | 11/2012 | Linn et al. |
| 2012/0277118 A1 | 11/2012 | Bhatia et al. |
| 2012/0277120 A1 | 11/2012 | Serber et al. |
| 2012/0277144 A1 | 11/2012 | Duckers |
| 2012/0277152 A1 | 11/2012 | Ringeisen et al. |
| 2012/0277155 A1 | 11/2012 | VanAntwerp et al. |
| 2012/0277156 A1 | 11/2012 | Gross et al. |
| 2012/0277157 A1 | 11/2012 | Hillman |
| 2012/0277161 A1 | 11/2012 | Agrez et al. |
| 2012/0277162 A1 | 11/2012 | Krasnoperov et al. |
| 2012/0277173 A1 | 11/2012 | Eidenberger |
| 2012/0277179 A1 | 11/2012 | Bhargava |
| 2012/0277195 A1 | 11/2012 | Banov et al. |
| 2012/0277203 A1 | 11/2012 | Lasley et al. |
| 2012/0277204 A1 | 11/2012 | Taniguchi et al. |
| 2012/0277205 A1 | 11/2012 | Badorc et al. |
| 2012/0277210 A1 | 11/2012 | Catron et al. |
| 2012/0277215 A1 | 11/2012 | Ksander et al. |
| 2012/0277228 A1 | 11/2012 | Sutton et al. |
| 2012/0277229 A1 | 11/2012 | Bearss et al. |
| 2012/0277251 A1 | 11/2012 | Palladino et al. |
| 2012/0277265 A1 | 11/2012 | Deraeve et al. |
| 2012/0277269 A1 | 11/2012 | Reilly |
| 2012/0277271 A1 | 11/2012 | Nadeson et al. |
| 2012/0277277 A1 | 11/2012 | Wallace et al. |
| 2012/0277279 A1 | 11/2012 | Barnett et al. |
| 2012/0277282 A1 | 11/2012 | Gotthardt et al. |
| 2012/0277288 A1 | 11/2012 | Drumm et al. |
| 2012/0277307 A1 | 11/2012 | Waddell |
| 2012/0277309 A1 | 11/2012 | Gass et al. |
| 2012/0277312 A1 | 11/2012 | Mink et al. |
| 2012/0277316 A1 | 11/2012 | Tillman et al. |
| 2012/0277319 A1 | 11/2012 | Steigerwald et al. |
| 2012/0277324 A1 | 11/2012 | Burk et al. |
| 2012/0277364 A1 | 11/2012 | Lolli et al. |
| 2012/0277376 A1 | 11/2012 | Baker, Jr. et al. |
| 2012/0277382 A1 | 11/2012 | Booth et al. |
| 2012/0277412 A1 | 11/2012 | Furusako et al. |
| 2012/0277430 A1 | 11/2012 | Taniguchi et al. |
| 2012/0277431 A1 | 11/2012 | Taniguchi et al. |
| 2012/0277451 A1 | 11/2012 | Ochiai |
| 2012/0277453 A1 | 11/2012 | Franklin et al. |
| 2012/0277517 A1 | 11/2012 | Ivkov et al. |
| 2012/0277521 A1 | 11/2012 | Chamberlin |
| 2012/0277522 A1 | 11/2012 | Shalon et al. |
| 2012/0277523 A1 | 11/2012 | Shalon et al. |
| 2012/0277537 A1 | 11/2012 | Kucklick et al. |
| 2012/0277544 A1 | 11/2012 | Fernandes et al. |
| 2012/0277546 A1 | 11/2012 | Soykan et al. |
| 2012/0277567 A1 | 11/2012 | Harlev et al. |
| 2012/0277572 A1 | 11/2012 | Hubbard |
| 2012/0277574 A1 | 11/2012 | Panescu |
| 2012/0277576 A1 | 11/2012 | Lui |
| 2012/0277578 A1 | 11/2012 | Gunday et al. |
| 2012/0277582 A1 | 11/2012 | Mali |
| 2012/0277584 A1 | 11/2012 | Tanaka et al. |
| 2012/0277592 A1 | 11/2012 | Zelenka et al. |
| 2012/0277599 A1 | 11/2012 | Greenhut |
| 2012/0277600 A1 | 11/2012 | Greenhut |
| 2012/0277618 A1 | 11/2012 | Giftakis et al. |
| 2012/0277621 A1 | 11/2012 | Gerber et al. |
| 2012/0277624 A1 | 11/2012 | Cucin |
| 2012/0277626 A1 | 11/2012 | Burbank et al. |
| 2012/0277638 A1 | 11/2012 | Skelton et al. |
| 2012/0277639 A1 | 11/2012 | Pollock et al. |
| 2012/0277642 A1 | 11/2012 | Smith et al. |
| 2012/0277668 A1 | 11/2012 | Chawla |
| 2012/0277671 A1 | 11/2012 | Fuentes |
| 2012/0277672 A1 | 11/2012 | Pepper et al. |
| 2012/0277674 A1 | 11/2012 | Clark, III et al. |
| 2012/0277693 A1 | 11/2012 | Bailey |
| 2012/0277716 A1 | 11/2012 | Ali et al. |
| 2012/0277718 A1 | 11/2012 | Campbell et al. |
| 2012/0277720 A1 | 11/2012 | Humes et al. |
| 2012/0277725 A1 | 11/2012 | Kassab et al. |
| 2012/0277729 A1 | 11/2012 | Melsheimer |
| 2012/0277730 A1 | 11/2012 | Salahieh et al. |
| 2012/0277736 A1 | 11/2012 | Francischelli |
| 2012/0277740 A1 | 11/2012 | Warnking et al. |
| 2012/0277741 A1 | 11/2012 | Davalos et al. |
| 2012/0277743 A1 | 11/2012 | Vallittu |
| 2012/0277746 A1 | 11/2012 | Morgan et al. |
| 2012/0277749 A1 | 11/2012 | Mootien et al. |
| 2012/0277752 A1 | 11/2012 | Wasielewski |
| 2012/0277753 A1 | 11/2012 | Linderman et al. |
| 2012/0277756 A1 | 11/2012 | Ray et al. |
| 2012/0277766 A1 | 11/2012 | Ferree |
| 2012/0277770 A1 | 11/2012 | Fenton et al. |
| 2012/0277771 A1 | 11/2012 | Vaz et al. |
| 2012/0277772 A1 | 11/2012 | Aben et al. |
| 2012/0277773 A1 | 11/2012 | Sargeant et al. |
| 2012/0277774 A1 | 11/2012 | Guo |
| 2012/0277776 A1 | 11/2012 | Kraemer et al. |
| 2012/0277781 A1 | 11/2012 | Gertner |
| 2012/0277784 A1 | 11/2012 | Berez et al. |
| 2012/0277785 A1 | 11/2012 | Aggerholm et al. |
| 2012/0277786 A1 | 11/2012 | Mohl |
| 2012/0277791 A1 | 11/2012 | Abo-Auda et al. |
| 2012/0277792 A1 | 11/2012 | Teeslink et al. |
| 2012/0277793 A1 | 11/2012 | Marczyk et al. |
| 2012/0277798 A1 | 11/2012 | Benson et al. |
| 2012/0277800 A1 | 11/2012 | Jackson |
| 2012/0277807 A1 | 11/2012 | Myung et al. |
| 2012/0277811 A1 | 11/2012 | Lauchner et al. |
| 2012/0277812 A1 | 11/2012 | Kraus |
| 2012/0277814 A1 | 11/2012 | Schuler |
| 2012/0277820 A1 | 11/2012 | Wu et al. |
| 2012/0277823 A1 | 11/2012 | Gerber et al. |
| 2012/0277825 A1 | 11/2012 | Mawson et al. |
| 2012/0277833 A1 | 11/2012 | Gerber et al. |
| 2012/0277835 A1 | 11/2012 | Della Santina et al. |
| 2012/0277837 A1 | 11/2012 | Schuler |
| 2012/0277843 A1 | 11/2012 | Weber et al. |
| 2012/0277845 A1 | 11/2012 | Bowe |
| 2012/0277846 A1 | 11/2012 | Schreck et al. |
| 2012/0277852 A1 | 11/2012 | Shukla et al. |
| 2012/0277853 A1 | 11/2012 | Rothstein |
| 2012/0277854 A1 | 11/2012 | Ryan |
| 2012/0277855 A1 | 11/2012 | Lashinski et al. |
| 2012/0277856 A1 | 11/2012 | Spenser et al. |
| 2012/0277862 A1 | 11/2012 | Tornier et al. |
| 2012/0277864 A1 | 11/2012 | Brodke et al. |
| 2012/0277865 A1 | 11/2012 | Trieu et al. |
| 2012/0277867 A1 | 11/2012 | Kana et al. |
| 2012/0277872 A1 | 11/2012 | Kana et al. |
| 2012/0277873 A1 | 11/2012 | Kana et al. |
| 2012/0277879 A1 | 11/2012 | Ripamonti |
| 2012/0277880 A1 | 11/2012 | Winslow et al. |
| 2012/0277882 A1 | 11/2012 | Huang et al. |
| 2012/0277896 A1 | 11/2012 | Uekita et al. |
| 2012/0277903 A1 | 11/2012 | Schaefer |
| 2012/0277939 A1 | 11/2012 | Kumar |
| 2012/0277940 A1 | 11/2012 | Kumar et al. |
| 2012/0277949 A1 | 11/2012 | Ghimire et al. |
| 2012/0277979 A1 | 11/2012 | Kato et al. |
| 2012/0277998 A1 | 11/2012 | Bevilacqua et al. |
| 2012/0277999 A1 | 11/2012 | Somogyi et al. |
| 2012/0278032 A1 | 11/2012 | Chen |
| 2012/0278098 A1 | 11/2012 | Vovan et al. |
| 2012/0278099 A1 | 11/2012 | Kelly et al. |
| 2012/0278123 A1 | 11/2012 | Houle |
| 2012/0278144 A1 | 11/2012 | Popilock et al. |
| 2012/0278195 A1 | 11/2012 | Joseph |
| 2012/0278200 A1 | 11/2012 | van Coppenolle et al. |

(56) References Cited

U.S. PATENT DOCUMENTS

| | | |
|---|---|---|
| 2012/0278236 A1 | 11/2012 | Jain et al. |
| 2012/0278242 A1 | 11/2012 | Griffith |
| 2012/0278411 A1 | 11/2012 | Lavine |
| 2012/0278439 A1 | 11/2012 | Ahiska et al. |
| 2012/0278454 A1 | 11/2012 | Stewart et al. |
| 2012/0278484 A1 | 11/2012 | Westphal |
| 2012/0278520 A1 | 11/2012 | Barrenscheen et al. |
| 2012/0278554 A1 | 11/2012 | Eilert |
| 2012/0278592 A1 | 11/2012 | Tran |
| 2012/0278597 A1 | 11/2012 | De Atley et al. |
| 2012/0278654 A1 | 11/2012 | Shen et al. |
| 2012/0278657 A1 | 11/2012 | Baker et al. |
| 2012/0278676 A1 | 11/2012 | Teraura |
| 2012/0278684 A1 | 11/2012 | Eldredge et al. |
| 2012/0278689 A1 | 11/2012 | Tamo et al. |
| 2012/0278760 A1 | 11/2012 | Cemy et al. |
| 2012/0278771 A1 | 11/2012 | Ren |
| 2012/0278799 A1 | 11/2012 | Starks et al. |
| 2012/0278865 A1 | 11/2012 | Sawdy |
| 2012/0278913 A1 | 11/2012 | Fraser |
| 2012/0278947 A1 | 11/2012 | Guo et al. |
| 2012/0278957 A1 | 11/2012 | Phan et al. |
| 2012/0283758 A1 | 11/2012 | Miller |
| 2013/0041395 A1 | 2/2013 | De Canniere |
| 2013/0066275 A1 | 3/2013 | De Canniere |

FOREIGN PATENT DOCUMENTS

| | | |
|---|---|---|
| EP | 1169968 | 1/2002 |
| EP | 1222896 | 7/2002 |
| EP | 1266626 | 12/2002 |
| EP | 1269919 | 1/2003 |
| EP | 1254634 | 7/2003 |
| EP | 1244725 | 7/2005 |
| EP | 1773239 B1 | 3/2010 |
| WO | WO 2012 040865 | 4/2012 |
| WO | WO2012040865 A1 | 4/2012 |
| WO | WO2012016398 A1 | 9/2012 |
| WO | WO2013/023016 | 2/2013 |
| WO | WO 2013036742 | 3/2013 |
| WO | WO2015081053 A1 | 6/2015 |

* cited by examiner

SYSTEM FOR TREATING HEART VALVE MALFUNCTION INCLUDING MITRAL REGURGITATION

BACKGROUND OF THE INVENTION

Field of the Invention

The present invention is directed to an intra-pericardial surgically introduced positioning structure that is disposed and structured to repetitively assume an expanded orientation and a contracted orientation. As such, a repetitively and temporarily "lifting" or "shaping" force is exerted on the exterior of the myocardium in synchronization with the heartbeat thereby positioning the leaflets of the mitral valve to close to a sufficient degree to eliminate or restrict mitral regurgitation.

Description of the Related Art

Figure 1:
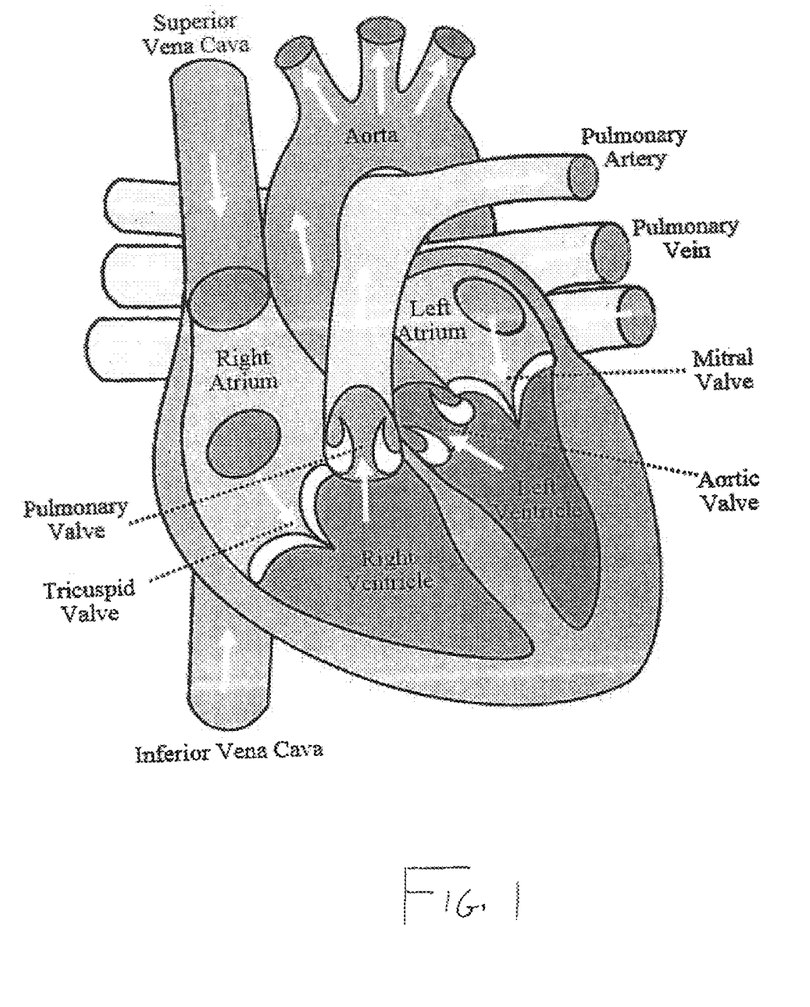

As clearly disclosed in the prior art schematic representation of FIG. 1, the human heart is a four chambered pump that moves blood efficiently through the vascular system. During normal operation, blood enters the heart through the vena cava and flows into the right atrium. Thereafter, blood flows from the right atrium through the tricuspid valve and into the right ventricle. Upon contraction of the right ventricle, blood is forced through the pulmonic or pulmonary valve and into the lungs for oxygenation. The oxygenated blood returns from the lungs and enters the heart through the left atrium and passes through the mitral valve into the left ventricle. Upon contraction of the left ventricle the blood therein flows through the aortic valve and into the aorta and throughout the vascular system.

As indicated, the mitral valve is disposed in flow regulating communication between the left atrium and the left ventricle. The structural and/or operative components of the mitral valve comprises two valve leaflets, the mitral valve annulus, which forms a ring that supports the valve leaflets; papillary muscles, which tether the valve leaflets to the left ventricle wall, thereby preventing them from prolapsing back into the left atrium. Chordae tendineae serve to connect the mitral valve leaflets to the papillary muscles thereby further preventing the leaflets from prolapsing back into the left atrium. A dysfunction of any of the described mitral valve apparatus can cause "mitral regurgitation". Mitral regurgitation is a disorder of the heart in which the leaflets of the mitral valve do not close properly when the heart pumps out blood. This abnormal leaking of blood from the left ventricle, through the mitral valve and, into the left atrium when the left ventricle contracts, results in the "regurgitation" of blood back into the left atrium. It is generally recognized in the medical profession that mitral regurgitation is the second most common form of valvular heart disease.

As generally set forth above, when properly functioning, the anterior and posterior valve leaflets of the mitral valve overlap during contraction of the left ventricle and prevent blood from flowing back into the left atrium. This overlap of the two leaflets leaning upon each other is called the "coaptation" and absorbs most of the strain on the mitral apparatus during the ventricular contraction. However, when the mitral valve malfunctions, due to various cardiac diseases, the leaflets are no longer coapting resulting in the mitral valve remaining partially open during ventricular contraction. In turn this allows the aforementioned "regurgitation" of the blood back into the left atrium, as generally set forth above. When the mitral valve does not close hermetically during the ventricular contraction, the aforementioned back flow of blood to the atrium and the pulmonary vasculature, results in a deleterious condition. More specifically, this condition increases the work load to the heart and may lead to heart failure.

The mitral valve is intended to open fully so as to provide no resistance to the blood stream progressing from the left atrium (LA) into the left ventricle (LV) during diastoly (the ventricular relaxation phase) and to close fully during the systoly (the ventricular ejection phase) so as to prevent the blood from flowing back into the atrium and into the pulmonary venous circulation. The role of the mitral valve is therefore to ensure antegrade progression of the blood through the left cardiac chambers. It works in synchrony with the three other heart valves that are ensuring the same function between the right atrium (RA) i.e. the pulmonic valve and downstream to the mitral valve, between the left ventricle and the aorta i.e. the aortic valve at the junction.

From a mechanical standpoint the mitral valve has to face high gradients of pressure during the ventricular contraction to hold up against a pressure head of about 100 mm of mercury (Hg) or more, which is substantially the peak pressure in the LV being usually superior or equal to 110 mmHg and the one in the atrium around 8 mmHg. This strain is absorbed mostly by the coaptation of the two mitral leaflets when closed, leaning on each other with a contact height around 10 mm over the entire length of the mitral coaptation line. The coaptation of the leaflets depends on the adequate anatomy (integrity of their structures) and adequate function of 5 components, which are 1. the mitral annulus, 2. the anterior and posterior leaflets, 3. the mitral chordae, 4. the papillary muscles (PPM) and 5. the ventricular walls themselves. Any congenital malformation or acquired lesion of one or more of these components can lead to a mitral insufficiency—also known as mitral regurgitation (MR) or, as emphasized herein, a failure of the mitral valve to hermetically close during the ventricular contraction and the leaking of a variable amount of blood back into the LA.

This situation is correlated with a poor outcome for the patient, since it increases the workload to the heart, as well as it increases the left atrial and ventricular chambers volumes. Furthermore, the existence of severe mitral regurgitation and ventricular dilation generate a vicious cycle in which MR begets more MR. Indeed, when the ventricle increases in size the distance between the papillary muscles increases, tethering the mitral chordae and impeding their full motion up to the plane of the annulus. This pathophysiological continuum leads to heart failure, pulmonary hypertension, atrial fibrillation and ultimately death.

Known treatment for MR comprises the administration of pharmacological drugs and the fixing the regurgitation by either, a surgical repair (the vast majority of the cases >98%) including a surgical repair or replacement of the valve or in some selected cases, using an emerging percutaneous technology that is still under evaluation (the Mitraclip®). Although there is a considerable trend to fix the MR as early as possible in its natural course, the indication and timing of the intervention rely also on the etiology of the condition, as well as on the functional anatomy and structural damage to the valve and the ventricle.

One particular case of mitral regurgitation targeted by the present invention is called ischemic mitral regurgitation (IMR). Ischemia to the heart relates to an insufficient blood supply to the myocardium because of narrowed (stenosed) coronary arteries. This condition is extremely prevalent and the number one killer in the USA. The natural history of coronary artery disease (stenosis) is to evolve towards acute vessel occlusion leading to acute myocardial infarction (myocardial necrosis i.e. cellular death secondary to cellular asphyxia in the territory irrigated by the occluded artery). The onset of mitral ischemia is a very bad prognostic factor in the acute phase of myocardial infarction.

Repairing ischemic mitral insufficiency poses particular problems and challenges that have been approached in different ways. However, many of such approaches have been disappointing on the very mid-term, with most studies reporting ≥40% of failure rate only two years after the surgery. Most of the proposed solutions are targeted towards the annulus and the leaflets although the mitral valve apparatus is anatomically normal and the functional problem is of ventricular origin. Indeed, the scar tissue replacing the death of the myocardium during the body repair process is immobile and remains distended in systoly. Therefore, by tethering as above-mentioned, the mobility of the entire mitral apparatus attached to it is impaired resulting in the PPM, the chordae and the leaflets being pulled "down" or away from the plane of the mitral annulus. This impeaches the leaflet (usually the posterior leaflet) to reach the point where it should coapt with its anterior counterpart. More technically, this mechanism corresponds to a type IIIb according to Carpentier's classification. It is an extremely frequent phenomenon.

Similarly other, "non-ischemic" etiologies leading to mitral regurgitation, such as for example idiopathic cardiomyopathy, could benefit from the implementation and practice of one or more to the embodiments of the present invention, as described in detail herein. An alternative solution allowing an easier, safer and possibly more durable reduction or disappearance of the mitral regurgitation has been sought, based on the premise that the IMR is a "ventricular disease" thereby suggesting a ventricular solution rather than concentrating on an approach to a normal annulus or normal leaflet.

Accordingly, there is a need in the medical arts for appropriate instrumentation, method and/or system of overcoming heart valve malfunctions, specifically including mitral regurgitation, as described above.

SUMMARY OF THE INVENTION

The present invention is directed to an intra-pericardial surgically introduced positioning structure that is disposed between the inner surface of the pericardium and the outer surface of the myocardium. Moreover, the positioning structure is operative to repetitively assume an expanded orientation and a contracted orientation. As such, structural and operative features of the positioning structure serve to repetitively and temporarily exert a "lifting" or "shaping" force on the exterior of the myocardium, specifically in the area of the ventricular wall supporting the tethered papillary muscle. The delivery of such a temporary and repetitive lifting or shaping force, in synchronization with the heartbeat or cardiac cycle, enable one of the mitral leaflets, typically a tethered posterior leaflet, to meet its anterior counterpart and coapt to a sufficient degree to eliminate or restrict mitral regurgitation. For purposes of clarity, the terms "lifting force" or "shaping force" or their equivalents are compatible in that the force exerted on the heart will temporarily and repetitively at least partially change the "shape" of the heart to the extent of "lifting" the left ventricular wall in a manner which facilitates a positioning of at least one of the mitral leaflets into a coapting relation with the other mitral leaflet.

Accordingly, the positioning structure is structured and operative to assume the expanded orientation and the contracted orientation on a repetitive basis in synchronization with the heartbeat. During the expanded orientation, the position the affected mitral leaflet is forced into a closed position during systoly and prevents or significantly restricts mitral regurgitation. Further, the positioning structure may be in the form of a flexible and/or expandable material bladder or "balloon", which is capable of being inflated and deflated to assume the expanded and contracted orientations respectively.

A retaining assembly is positioned and structured to operatively dispose the positioning structure in moveably supporting relation to an exterior wall portion of the heart. As set forth above and in more specific terms, the retaining assembly and the positioning structure are cooperatively disposed, dimensioned and structured to operatively dispose the positioning structure in supporting and force exerting position relative to the ventricular wall portion with supports the tethered papillary muscle. Upon assumption of the positioning structure in the expanded orientation, the exertion of the lifting and shaping force is sufficient in degree and direction to enable the tethered posterior leaflet, or other affected leaflet, to meet its counterpart leaflet of the mitral valve and assume a sealing relation therewith.

Accordingly, at least one embodiment of the retaining assembly includes at least one substantially semi-rigid guide wire or like structure, having sufficient flexibility to be guided or maneuvered into a position about the ventricular wall or the large vessels of the cardiac outflow tracks, through the transfer sinus (sinus Theild). However, in at least one additional preferred embodiment the retaining assembly may include a retaining structure in the form of a net-like sack, sock or bag structure and/or configuration. Further, the net, sack, etc., is preferably formed from an open mesh material comprising a plurality of strands connected in at least partially spaced relation to one another. As such, the open mesh material of the retaining structure is dimensioned so as to at least partially overlie, enclose and/or surround the biventricular wall of the myocardium. In such a preferred position or orientation, the open mesh retaining structure will serve to dispose the expandable and contractible positioning structure in an appropriate position relative to the aforementioned ventricular wall associated with the tethered papillary muscle. In such position and as set forth above, the positioning structure will exert sufficient force, when expanded, to effectively "lift" the affected mitral leaflet into closing relation to the counterpart leaflet of the mitral valve.

When the positioning structure is in the form of the aforementioned inflatable structure such as, but not limited to, a bladder or balloon, a pump assembly is operatively associated therewith. More specifically the pump assembly and/or the main body of the pump is dimensioned and configured to be surgically inserted and maintained within the chest cavity in fluid communication with the inflatable positioning structure. Moreover, the pump assembly is structured, in cooperation with other operative components of the system of the present invention, to cause and regulate the inflation and deflation of the inflatable retaining structure in a manner which corresponds to and/or is synchronized with the intended heartbeat or cardiac cycle.

In yet another embodiment, at least a portion of the positioning structure comprises or is at least partially defined by the strands of the open mesh retaining structure. In such an embodiment, at least some of the strands are inflatable thereby enabling the transverse dimension or diameter of certain ones of the plurality of strands to expand and contract in accordance with their being inflated and deflated. In this embodiment, the pump is disposed in fluid communication with the plurality of inflatable/deflatable strands of the open mesh material, which may be used in combination with the inflatable and deflatable or expandable/contractible positioning structure. In contrast, the open mesh material comprising a plurality of inflatable strands may be used independent of any type of expandable or contractible positioning member. Therefore, the retaining structure may define an expandable or contractible positioning member to the extent of causing a "shape variance" of the myocardium. As indicated such a shape variance is applied to the extent of providing a lifting and/or positioning force on the ventricular wall associated with the tethered papillary muscle in order to lift or reposition an affected leaflet of the mitral valve into a closed orientation with its counterpart leaflet.

As emphasized, the heart shape varying force exerted on the heart wall by the expandable/contactable positioning structure, in its different forms described herein, should be synchronized with the heartbeat or cardiac cycle. Accordingly, the aforementioned pump assembly is operable in combination with an activating assembly connected to at least the retaining structure in an operative relation to the heart. The activating assembly is structured to detect electrical activity of the heart and as such may comprise a plurality of electrodes connected to the open mesh material of the retaining structure or other portions of a different embodiment of the retaining structure in a manner which detects such electrical activity.

In addition, the plurality of electrodes are operatively disposed in a predetermined array relative to the heart so as to facilitate the activating assembly having both "sensing" capabilities and "pacing" capabilities. As such, the sensing capabilities are operative to synchronize the expansion and contraction of the positioning structure so as to coincide with the cardiac cycle, as indicated above. Moreover, the pacing capabilities are operative to stimulate the heart into a biventricular resynchronization pacing. As used herein, the term "biventricular synchronization" is meant to include the stimulating or "pacing" of the heart in a manner that left and right ventricles expand and contract in a manner which facilitates normal or acceptable blood flow through the heart in accordance with a normal or acceptable cardiac cycle.

In order to accomplish the aforementmentioned sensing and pacing capabilities the activating assembly further comprises and/or is associated with a processor, electrically connected to the plurality of electrodes and to the operative circuitry associated with a processor. Therefore the combined circuitry of the processor, as well as the other operative components of the activating assembly, are operatively determinative of the sensing capabilities and facilitate the synchronized expansion and contraction of the positioning structure and/or the expansion and contraction of the inflatable strands of the retaining structure, dependent on the embodiment utilized.

Therefore, the system and the operative components associated therewith as well as the method of application for eliminating or restricting the occurrence of mitral regurgitation include the exertion of a force on the exterior of the heart wall thereby temporarily and repetitively providing "shape variance" of the heart. The variance in the shape of the heart will be caused by an effective "lifting" or positioning action exerted by an expansion of the positioning structure such that an affected leaflet such as, but not limited to, the posterior mitral valve leaflet, is lifted or positioned into a substantially sealing and/or closing engagement with its counterpart leaflet.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a schematic representation of a normally functioning human heart and a representation of blood flow there through.

Like reference numerals refer to like parts throughout the several views of the drawings.

DETAILED DESCRIPTION OF THE PREFERRED EMBODIMENT

As represented in the accompanied drawings, the present invention is directed to a system for treating heart valve malfunction specifically including mitral regurgitation, wherein the various operative structural components are represented throughout FIGS. 2 through 5. For purpose of clarity a representative human heart is generally indicated as 100 and is surrounded and/or enclosed by a pericardium 102, wherein the operative and structural components of the system of the present invention are located within the interior of the chest cavity 104. In providing a clear perspective of the environment in which the system of the present invention is practiced, the outer chest wall 106, chest cavity 104, pericardium 102 and heart 100 are all represented in schematic form.

In more specific terms, the system of the present invention is directed to an intra-pericardial, surgically introduced positioning structure 10 located between the inner surface of the pericardium 102 and the outer surface of the heart wall as explained in greater detail hereinafter. As such, the positioning structure 10 is operative to assume an expanded orientation and a contracted orientation. Therefore, the positioning member, in at least one preferred embodiment, may be in the form of an inflatable structure as at 10' represented in FIGS. 4 and 5.

Moreover, the inflatable structure 10' may be in the form of a flexible, inflatable material such as, but not limited to, a bladder or balloon structure. Moreover, the inflation and deflation of the positioning structure 10' serves dispose it in the aforementioned aforementioned expanded and contracted orientations respectively. In cooperation therewith, a pump assembly generally indicated as 12 may disposed in fluid communication, as at 14, with the inflatable positioning member 10' so as to cause its inflation/deflation and/or a disposition into the expanded and/or contracted orientation.

Figure 2:
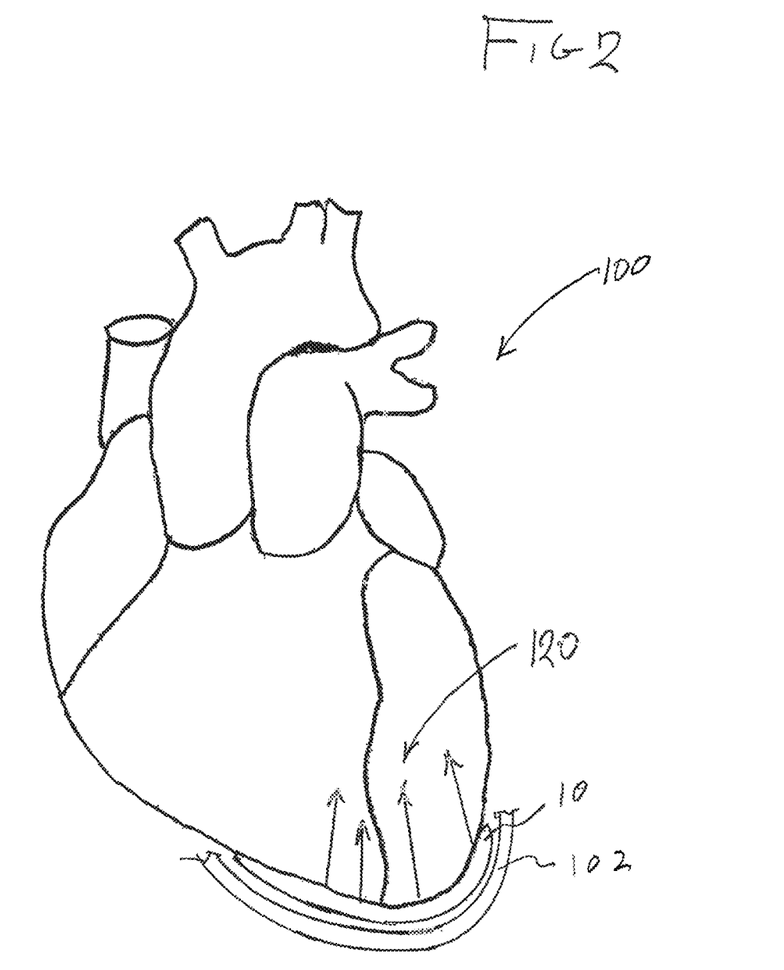
FIG. 2 is a schematic representation of an exterior view of the human heart with a positioning structure of the present invention operatively disposed relative thereto.
Figure 2A:
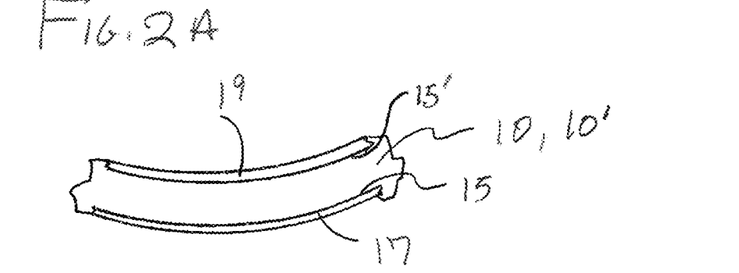
FIG. 2A is a schematic detailed view in partial cutaway of a portion of the positioning structure at least as represented to FIG. 2.

Due to its intended positioning between the inner surface of the pericardium 102 and the outer surface of the myocardium or heart wall in a preferred location, the exterior surface portions of positioning member 10 may be structured to facilitate engagement with the respective surfaces. As schematically represented in FIG. 2A, the positioning member 10 and/or 10' include a first and second outer surface 15 and 15' structured to facilitate an operative, intended engagement with the inner pericardial surface of the pericardium 102 and the exterior surface of the myocardium or wall of the heart 100. Therefore, a first surface portion 15 comprises a coating or other appropriate structure 17, which facilitates a gripping engagement with the inner pericardial surface. In contrast, the second surface portion 15' also includes a structural modification such as a second coating 18, which is structured to establish a substantially smooth or non-frictional engagement with the exterior surface of the heart wall. Intended disposition in an operative, force delivering relation of the positioning member 10 or 10' is facilitated by the provision of a retaining assembly, generally indicated as 20 in FIGS. 3, 4, and 5.

Figure 3:
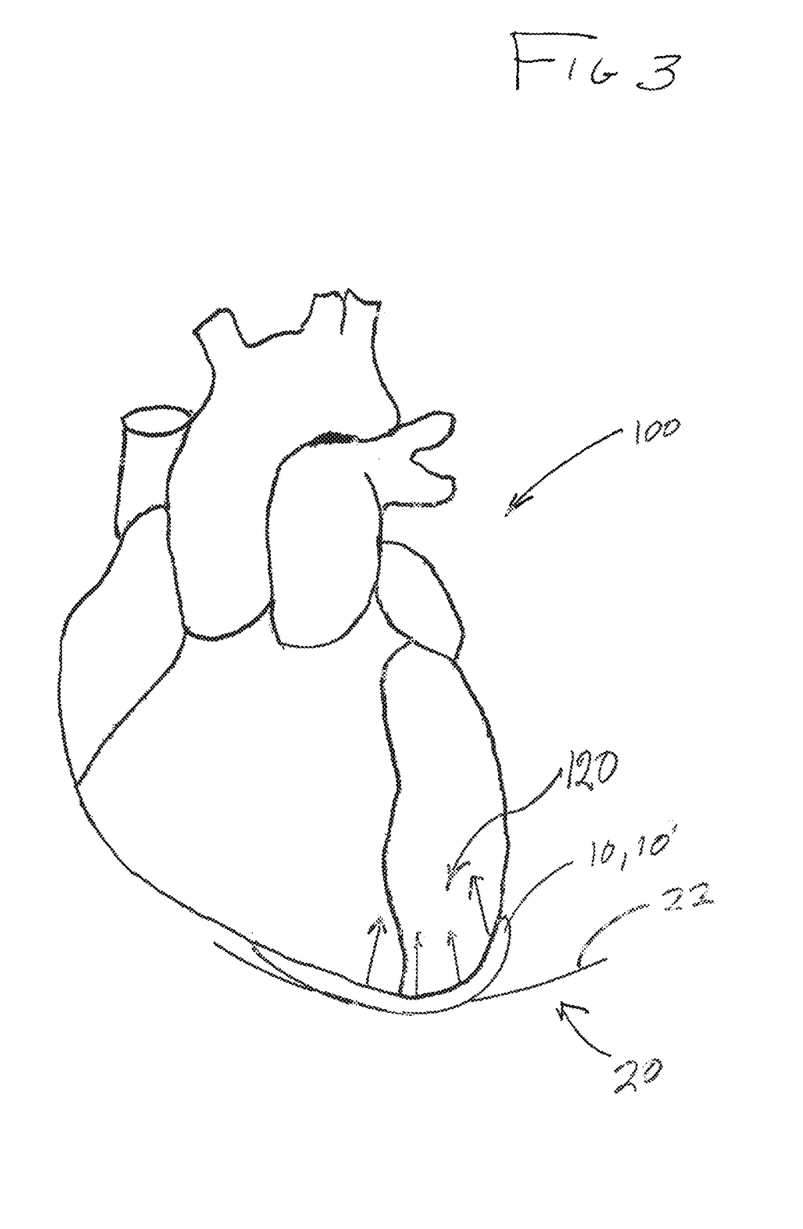
FIG. 3 is a schematic representation of an an exterior view of the human heart with the positioning structure of the embodiment of FIGS. 2 and 2A disposed in an operative position in combination with one embodiment of a retaining assembly.

More specifically, in the embodiment of FIG. 3, the retaining assembly 20 includes a retaining structure in the form of at least one semi-rigid guide wire 22 or like structure having sufficient flexibility and appropriate structural integrity that it can be maneuvered around the ventricular wall of the heart and/or the large vessels of the cardio-outflow tracks, such as through the transverse sinus. It is noted that FIG. 3 represents a single guide wire is 22. However, one or more of such guide wires or other appropriately equivalent structures may be utilized to position and maintain the positioning member 10 or 10' in an intended position' Such an intended, operative position facilitates the exertion of a sufficient and properly directed force 120 on the heart 100 to temporarily and repetitively cause a shape variance of the heart 100. Further, the appropriate force 120 exerted on the heart 100 is sufficiently and accurately directed to apply a lifting or positioning force to the ventricular wall 110 supporting the tethered papillary muscle. As a result, an affected leaflet, in at least some specific applications the tethered posterior leaflet, will be lifted or positioned into coapting or closing relation to the anterior or counterpart leaflet of the mitral valve.

With additional reference to the prior art schematic representation of FIG. 1 both the anterior and posterior leaflets of the mitral valve are indicated in a properly closed or coapted relation to one another. Accordingly, a properly directed force 120 exerted on the exterior of the ventricular wall will cause a temporary variance in the shape of at least a portion of the heart. As a result, the ventricular wall associated with the tethered papillary muscle will be lifted or positioned, to the extent of lifting or positioning the affected leaflet of the mitral valve into the closed orientation, as generally represented in FIG. 1, to restrict or prevent mitral regurgitation.

As emphasized hereinafter repetitive lifting or exertion of force on the proper portion of the ventricular wall will be synchronized with the beating of the heart or cardiac cycle. Therefore, the affected mitral valve leaflet will be brought into closing relation with its counterpart leaflet on a regular and consistent basis in order to properly perform both systoly and dystoly of the heart during the cardiac cycle. Further, the lifting force is schematically represented in at least some of the accompanying Figures as directional arrows 120. As also emphasized, the lifting force 120 causes the temporary change in the shape of the heart 100 resulting in the lifting and positioning of the ventricular wall and leaflet of the mitral valve upon the intended expansion or inflation of the positioning member 10 or 10'.

Figure 4:
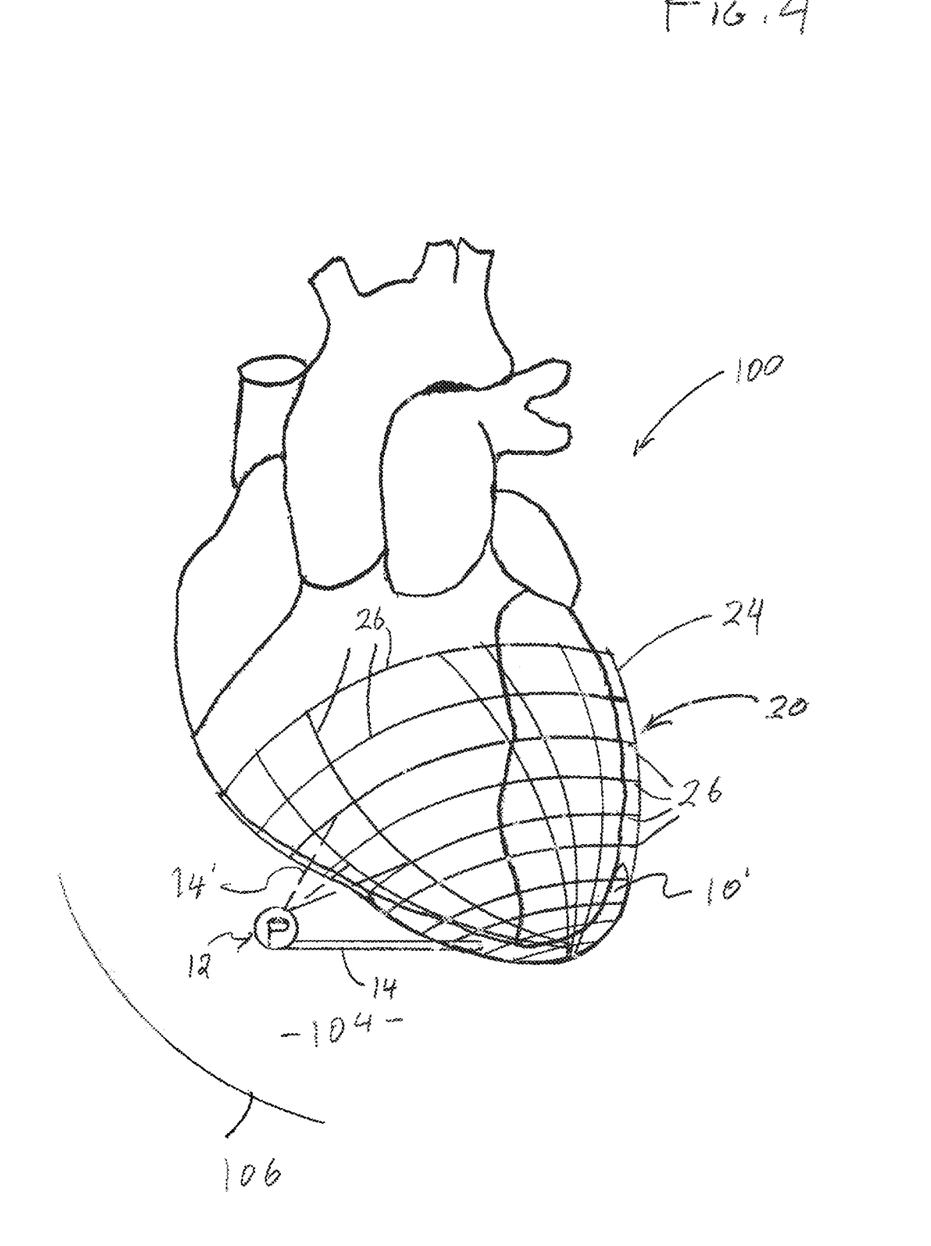
FIG. 4 is a schematic representation of an exterior view of the human heart with another preferred embodiment of the retaining assembly and associated retaining structure used in combination with the positioning structure of the embodiments of FIGS. 2 through 3.
Figure 5:
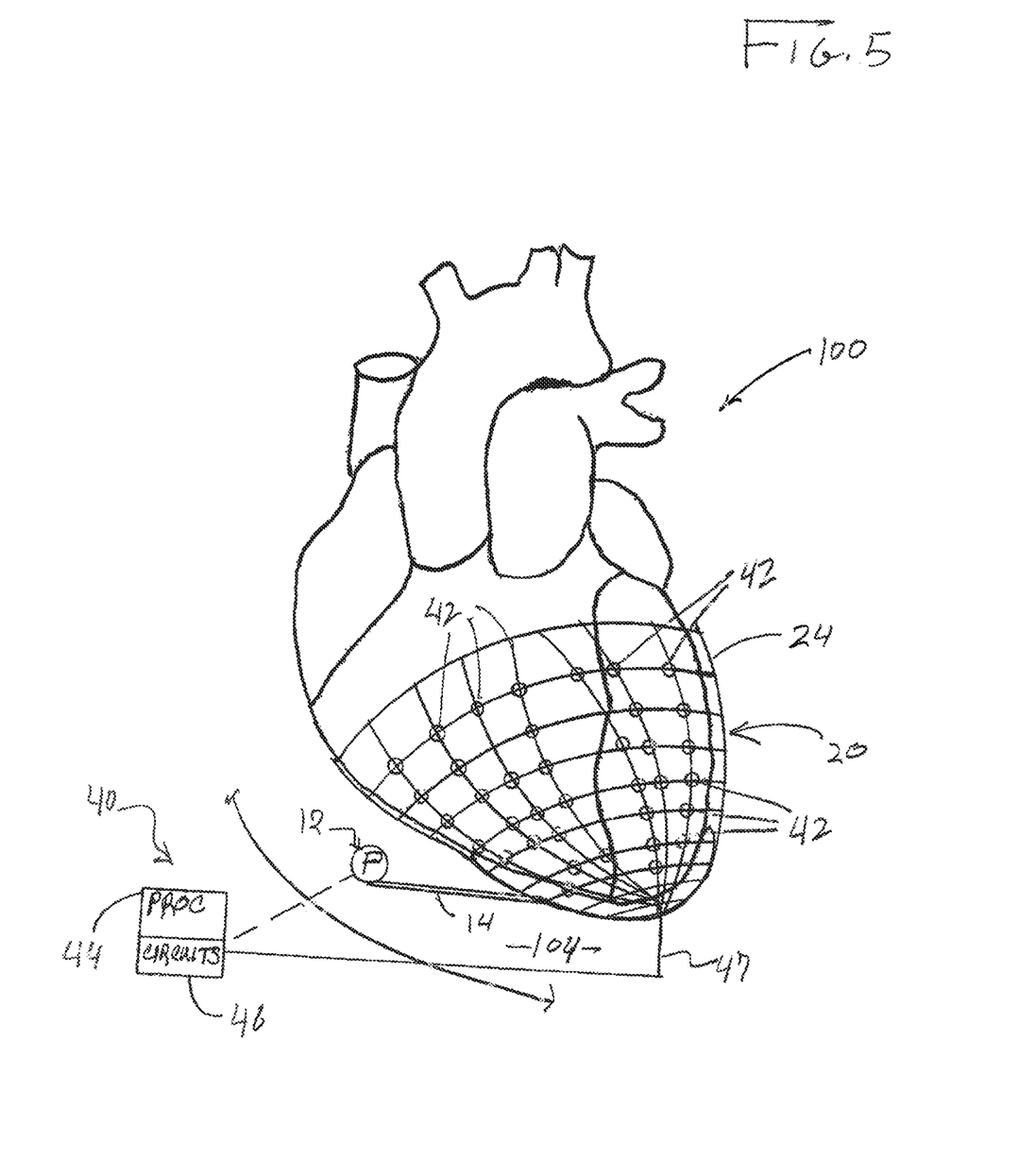
FIG. 5 is a schematic representation of yet another preferred embodiment of the positioning structure and retaining assembly of the embodiment of FIGS. 2 through 4 in further combination with an activating assembly.

The retaining assembly 20, as represented in FIGS. 4 and 5, defines yet another preferred embodiment, wherein the retaining structure 24 is dimensioned and configured to overlie, cover, or at least partially enclosed and/or surround the biventricular wall portion on the exterior of the heart 100. With reference to FIG. 1, the exterior of the biventricular wall is defined by the exterior wall portion surrounding or at least bounding a portion of both the right ventricle and the left ventricle. Accordingly, the retaining structure 24 may be in the form of a net-like device such as a net-like bag, sack, sock, etc. of sufficient dimension to enclose or surround the biventricular wall of the heart 100 as indicated above. Moreover, the retaining structure 24 may further comprise an open mesh configuration at least partially defined by a plurality of overlying, interconnected strands as at 26 at least partially disposed in spaced relation to one another. When the positioning assembly 10 or 10' is used in combination with the net-like retaining structure 24, it is disposed and maintained on the interior thereof when the positioning structure 10 or 10' assumes the expanded/inflated or contracted/deflated orientations. A sufficient and appropriate force 120 will thereby be exerted on the ventricular wall, primarily of the left ventricle which is tethered to the affected leaflet such as the posterior leaflet of the mitral valve, depicted in schematic form in FIG. 1.

With primary reference to FIG. 4 yet another preferred embodiment of the present invention may include at least some of the plurality of strands 26 of the retaining structure 24 being formed of an inflatable material and being connected to the pump assembly 12. As such, at least some of the plurality of strands 26 are inflated and deflated by activation and operation of the pump assembly 12. In such capacity the inflation/deflation of the plurality of strands 26 will effectively define these strands 26 as the aforementioned positioning member. In operation, the plurality of strands 26 repetitively and temporarily apply a lifting or positioning force 120 to at least the ventricular wall associated with a tethered papillary muscle of the affected leaflet of the mitral valve. As such the appropriate force 120 will be applied during the inflation of the plurality of strands 26.

Further, the inflatable strands 26 will be connected directly to the pump assembly 12 as at 14, and may be used in combination with an expandable and contactable positioning assembly 10 or 10' which itself may or may not be inflatable. In contrast, the structuring of the retaining structure 24 to have at least some of the strands 26 being inflatable may be used independently of the positioning structure 10 or 10'. Moreover, the inflation and deflation of the plurality of strands 26 effectively defines the positioning structure at least to the extent of exerting sufficient forces 120 on the exterior of the heart wall to accomplish the preferred lifting or positioning of the ventricular wall and repositioning of the prolapsing leaflet of the mitral valve.

With primary reference to FIG. 5, yet another preferred embodiment of the present invention comprises the retainer assembly 20, which may be in the form of the retaining structure 24 being directly associated with an activating assembly generally indicated as 40. Moreover, the activating assembly 40 comprises a plurality of electrodes 42 connected to or mounted on a plurality of the strands 26 of the retaining structure 24 and disposed in engaging and/or sensing relation to the exterior of the heart. As such, the plurality of electrodes 42 are disposed and structured to sense and determine electrical activity of the heart 100 and direct such data or information to a processor assembly 44. In turn, the processor 44 is operative in combination with appropriate circuitry 46 to accomplish both sensing capabilities and pacing capabilities. Therefore, the processor 44 and circuitry 46 is connected to the plurality of the electrodes 42, such that the electrical activity of the heart is detected and/or determined by the processor 44 and circuitry 46.

Therefore, the sensing capabilities associated with the activating assembly 40 are operative to synchronize the expansion and contraction of the positioning assembly 10, 10' with the heartbeat or cardiac cycle of the heart 100. As such, the expansion and/or inflation of the positioning structure 10, 10' and/or the inflatable strands 26 of the retaining structure 24 will exert an appropriate lifting or positioning of the ventricular wall of the heart in accordance with the ventricular ejection phase or systoly of the heart causing the closure of the mitral valve leaflets, thereby restricting or preventing mitral regurgitation. In turn, the aforementioned pacing capabilities of the activating assembly 40 are operative to stimulate the heart into a biventricular resynchronization in order to perform normal or adequate systoly/diastoly functioning of the heart in a prescribed manner. As further indicated, the processor 44 and/or circuitry 46 may be electrically connected to the plurality of electrodes 42, as at 47 either through a hardwire connection passing through the thoracic chamber 104 or otherwise be disposed on the interior thereof. Such an electrical connection may occur by a hardwire connection 47 or other wireless connection as appropriate.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A system for treating heart valve malfunction including mitral regurgitation, said system comprising;
   a positioning structure operative to assume an expanded orientation and a contracted orientation,
   a retaining assembly positioned and structured to dispose said positioning structure in moveably positioning relation to an exterior of a wall of a heart,
   said retaining assembly and a positioning member cooperatively disposed and structured to accomplish a shape variance of the heart, substantially concurrent to said expanded orientation of said positioning assembly, and
   said shape variance at least partially defining a position of a mitral valve into a predetermined orientation which restricts mitral regurgitation,
   wherein said retaining assembly comprises a retaining structure dimensioned and configured for disposition in at least partially covering relation to a biventricular mass of a myocardium,
   and wherein said retaining structure comprises an open mesh material including a plurality of strands disposed in at least partially spaced relation to one another, said strands collectively disposed in at least partially surrounding relation to the biventricular mass and concurrently in retaining relation to said positioning structure.

2. The system as recited in claim 1 wherein said predetermined orientation comprises a positioning of at least a portion of the mitral valve during systoly.

3. The system as recited in claim 2 wherein said predetermined orientation further comprises a dynamic positioning of portions of the mitral valve sufficient to facilitate diastolic filling.

4. The system as recited in claim 1 wherein said retaining assembly is positioned to operatively dispose said positioning structure in moveably supporting relation to the exterior of the wall of the heart, the wall of the heart comprising a ventricular wall of the heart, corresponding to a tethered papillary muscle.

5. The system as recited in claim 4 wherein said retaining assembly is configured to be disposed in engaging, retained relation with a biventricular mass of the heart.

6. The system as recited in claim 4 wherein said positioning structure comprises at least one inflatable member structured to respectively define said expanded and contracted orientation as an inflation and a deflation of said inflatable member.

7. The system as recited in claim 6 further comprising a pump assembly disposed in fluid communication with said at least one inflatable member, said pump assembly structured to regulate inflation and deflation of said one inflatable member.

8. The system as recited in claim 7 wherein said pump assembly comprises a sufficiently reduced dimension to facilitate operative placement thereof within a chest cavity.

9. The system as recited in claim 6 wherein said at least one inflatable member comprises a bladder at least partially formed of a flexible, inflatable material.

10. The system as recited in claim 1 wherein said retaining relation comprises said positioning structure disposed in a lifting relation to a ventricular wall corresponding to a capillary muscle tethered to the mitral valve, when said positioning structure is in said expanded orientation.

11. The system as recited in claim 1 wherein said positioning structure comprises at least some of said plurality of strands being inflated into said expanded orientation and deflatable into said contracted orientation.

12. The system as recited in claim 11 wherein said plurality of strands and a remainder of said retaining structure are configured to be cooperatively disposed and structured to exert a lifting force on the ventricular wall portion corresponding to a papillary muscle tethered to the mitral valve, when in, said expanded orientation; a lifting relation at least partially defining a shape variance of the heart including a positioning of the mitral valve into said orientation which restricts mitral regurgitation.

13. The system as recited in claim 1 wherein said positioning structure is operatively disposed between an inner surface of a pericardium and an outer surface of a myocardium.

14. The system as recited in claim 13 wherein said positioning structure comprises a first surface portion structured to facilitate predetermined operative engagement with an inner pericardial surface and a second surface portion structured to facilitate predetermined operative engagement with the outer surface of the myocardium.

15. The system as recited in claim 1 further comprising an activating assembly connected to said retaining structure in an operative relation to the heart, said activating assembly structured to detect electrical activity of the heart.

16. The system as recited in claim 15 wherein said activating assembly includes sensing capabilities operative to synchronize expansion and contraction of said positioning structure with a cardiac cycle.

17. The system as recited in claim 16 wherein said activating assembly includes pacing capabilities operative to stimulate the heart into biventricular resynchronization pacing.

18. The system as recited in claim 16 wherein said activating assembly comprises a plurality of electrodes connected to said retaining structure in at least partially spaced relation to one another.

19. The system as recited in claim 16 wherein said activating assembly further comprises a processor electrically connected to said plurality of electrodes and operatively determinative of said sensing capabilities and including said synchronized expansion and contraction of said retaining structure.

20. The system as recited in claim 19 wherein said processor is electrically connected to said plurality of electrodes and operatively determinative of said pacing capabilities.

21. A system for treating heart valve malfunction including mitral regurgitation, said system comprising;
   a positioning structure operative to assume an expanded orientation and a contracted orientation,
   a retaining assembly positioned and structured to dispose said positioning structure in moveably positioning relation to an exterior of a wall of a heart,
   said retaining assembly and said positioning structure cooperatively disposed and structured to accomplish a shape variance of the heart, substantially concurrent to said expanded orientation of said positioning structure, and
   said shape variance at least partially defining a positioning of a mitral valve into a predetermined orientation which restricts mitral regurgitation;
   wherein said positioning structure is operatively disposed between an inner surface of a pericardium and an outer surface of a myocardium;
   wherein said positioning structure comprises a first surface portion and a second surface portion respectively structured to facilitate predetermined operative engagement with an inner pericardial surface and the outer surface of the myocardium,
   wherein said first surface portion is structured to include a first coating structured to facilitate a gripping engagement with the inner pericardial surface.

22. The system as recited in claim 21 wherein said second surface portion is structured to include a second coating structured to facilitate a non-frictional engagement with the outer surface of the myocardium.

23. A system for treating mitral regurgitation comprising
   a positioning structure operative to assume an expanded orientation and a contracted orientation,
   a retaining structure disposed and structured to maintain said positioning structure within a pericardium in moveably positioning relation to a ventricular wall portion of a heart,
   a retaining assembly comprising said retaining structure dimensioned and configured for disposition in at least partially covering relation to a biventricular mass of a myocardium concurrently in retaining relation to said positioning structure,
   said positioning structure disposed in lifting relation to a ventricular wall portion corresponding to a papillary muscle tethered to a mitral valve, when said positioning structure is in said expanded orientation, and
   said lifting relation at least partially defining a shape variance of the heart including a positioning of the mitral valve into an orientation which restricts mitral regurgitation,
   wherein said positioning structure comprises at least one inflatable member structured to respectively define said expanded and contracted orientation as an inflation and a deflation of said one inflatable member,
   and wherein said retaining structure comprises an open mesh material including a plurality of strands disposed in at least partially spaced relation to one another, said strands collectively disposed in at least partially surrounding relation to the biventricular mass and concurrently in retaining relation to said positioning structure.

24. The system as recited in claim 23 further comprising an activating assembly connected in operative relation to the heart, said activating assembly structured to detect electrical activity of the heart including sensing capabilities operative to synchronize expansion and contraction of the retaining structure with the cardiac cycle.

25. The system as recited in claim 24 wherein said activating assembly includes pacing capabilities operative to stimulate the heart into biventricular resynchronization pacing.

26. The system as recited in claim 23 wherein said positioning structure is operatively disposed between an inner surface of the pericardium and an outer surface of the myocardium.

27. A system for treating mitral regurgitation comprising
   a positioning structure operative to assume an expanded orientation and a contracted orientation
   a retaining structure disposed and structured to maintain said positioning structure within a pericardium in moveably positioning relation to a ventricular wall portion of a heart,
   a retaining assembly comprising said retaining structure dimensioned and configured for disposition in at least partially covering relation to a biventricular mass of a myocardium concurrently in retaining relation to said positioning structure,
   said positioning structure disposed in lifting relation to a ventricular wall portion corresponding to a papillary muscle tethered to a mitral valve, when said positioning structure is in said expanded orientation, and
   said lifting relation at least partially defining a shape variance of the heart including a positioning of the mitral valve into an orientation which restricts mitral regurgitation;
   wherein said positioning structure is operatively disposed between an inner surface of the pericardium and an outer surface of the myocardium;
   wherein said positioning structure comprises first and second surface portions respectively including first and second coatings; said first and second coatings respectively structured to facilitate a gripping engagement with an inner pericardial surface and a non-frictional engagement with an outer surface of the myocardium.

* * * * *

UNITED STATES PATENT AND TRADEMARK OFFICE
CERTIFICATE OF CORRECTION

| | | |
|---|---|---|
| PATENT NO. | : 9,566,443 B2 | Page 1 of 1 |
| APPLICATION NO. | : 14/090383 | |
| DATED | : February 14, 2017 | |
| INVENTOR(S) | : Didier de Canniere | |

It is certified that error appears in the above-identified patent and that said Letters Patent is hereby corrected as shown below:

In the Claims

At Column 10, Line 50, Claim 12, please delete the "," after "in".

At Column 12, Line 37, Claim 27, please add a --,-- after "orientation".

Signed and Sealed this
Thirteenth Day of June, 2017

Joseph Matal
*Performing the Functions and Duties of the
Under Secretary of Commerce for Intellectual Property and
Director of the United States Patent and Trademark Office*